United States Patent [19]

Weiss

[11] Patent Number: 4,845,585

[45] Date of Patent: * Jul. 4, 1989

[54] ADJUSTABLE, CONDUCTIVE BODY STRAP

[75] Inventor: John W. Weiss, Austin, Tex.

[73] Assignee: Minnesota Mining and Manufacturing Company, St. Paul, Minn.

[*] Notice: The portion of the term of this patent subsequent to Jan. 19, 2005 has been disclaimed.

[21] Appl. No.: 134,820

[22] Filed: Dec. 18, 1987

Related U.S. Application Data

[63] Continuation-in-part of Ser. No. 37,616, Apr. 13, 1987, Pat. No. 4,720,765.

[51] Int. Cl.[4] .............................................. H05F 3/02
[52] U.S. Cl. .................................................... 361/220
[58] Field of Search ....................... 361/212, 220, 223; 24/265 C, 265 WS, 519, 271, 198, 169

[56] References Cited

U.S. PATENT DOCUMENTS

| 3,063,447 | 11/1962 | Kirsten | 361/220 X |
|---|---|---|---|
| 3,857,397 | 12/1974 | Brosseau | 361/220 |
| 4,038,726 | 8/1977 | Takahayashi | 24/198 |
| 4,373,175 | 2/1983 | Mykkanen | 361/220 |
| 4,398,277 | 8/1983 | Christiansen et al. | 361/220 |
| 4,402,560 | 9/1983 | Swainbank | 439/37 |
| 4,459,633 | 7/1984 | Vandermark | 361/220 |
| 4,475,141 | 10/1984 | Antonevich | 361/220 |
| 4,540,271 | 9/1985 | Rakov | 361/220 X |
| 4,577,256 | 3/1986 | Breidegam | 361/220 |
| 4,596,053 | 6/1986 | Cohen et al. | 361/212 X |
| 4,662,695 | 5/1987 | Gordon et al. | 361/220 |
| 4,676,561 | 1/1987 | Barrett, II | 361/220 X |
| 4,720,765 | 1/1988 | Weiss | 361/220 |

Primary Examiner—L. T. Hix
Assistant Examiner—Brian W. Brown
Attorney, Agent, or Firm—Donald M. Sell; Walter N. Kirn; William D. Bauer

[57] ABSTRACT

An adjustable, conductive body strap utilizing a connector securing a strip of material held in a closed loop with a mechanical connector with the interior surface of the strip of material being electrically conductive. An electrical connector connects the conductive surface of the strip of material to a connection point to provide for external electrical ground connection. The mechanical connector secures one end of the strip of material in place. The connector adjustably secures the opposite end of the strip of material utilizing a recess into which a plate is mounted with a plurality of spikes. The strip of material is impaled upon the plurality of spikes. A cover, preferably hinged, then secures the strip of material over the plurality of spikes once it is suitably adjusted completing the adjustable connection. An electrically conductive back plate connects both ends of the strip of material to the electrical connection point.

17 Claims, 3 Drawing Sheets

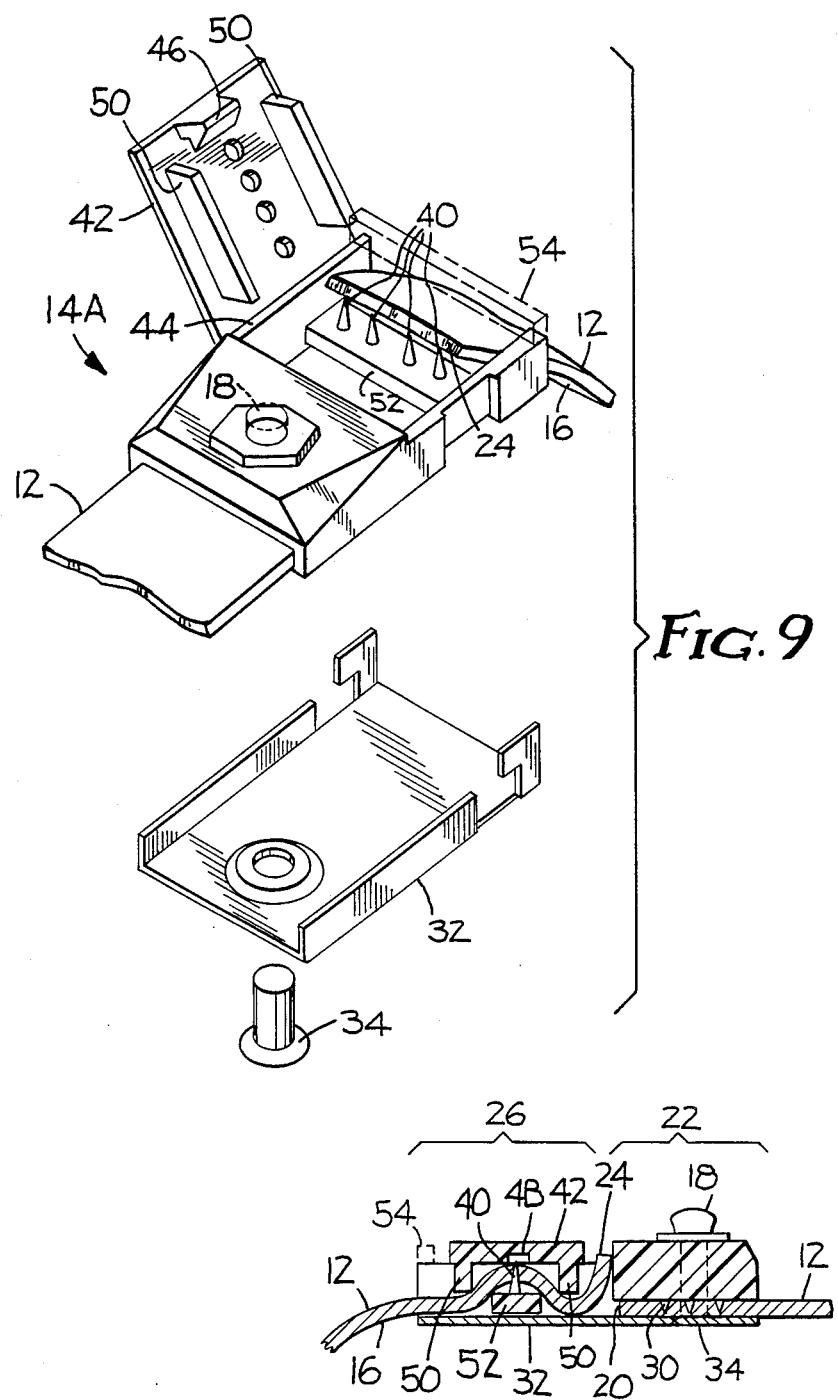

ADJUSTABLE, CONDUCTIVE BODY STRAP

RELATED APPLICATIONS

The present application is a continuation-in-part of U.S. Ser. No. 07/037,616, now U.S. Pat. No. 4720765 John Walter Weiss, Adjustable, Conductive Body Strap, filed Apr. 13, 1987.

BACKGROUND OF THE INVENTION

The present invention relates generally to electrically conductive body straps and more particularly to electrically conductive body straps which are adjustable.

The buildup of electrostatic charges and their subsequent discharge is a significant problem in certain industries. Individuals working in an everyday work environment commonly may develop thousands of volts of electrostatic charge potential by, as an example, walking across carpeting or moving dissimilar objects against each other. An individual, or object, so charged presents a severe hazard in certain environments. One example is an explosive environment where the danger is inherently obvious. Another example is the electronic integrated circuit (component) industry. The charged individual or object may discharge near or through an electrostatic sensitive electronic component. For example, an individual who is electrostatically charged may hold an electrostatic sensitive component and then lay the component on a surface, e.g., a grounded work surface, at a different potential from the individual. At the instant of contact, a potential difference of thousands of volts exists across the component, from the electrostatically charged individual to the grounded work surface. The current passing through or near, due to the electric field generated, may damage the component. The damage caused to the component may cause it to fail immediately or, worse, could degrade the operating characteristics or the reliability of the component. The result is either expensive rework or, worse, the existence of substandard or subreliable equipment in the field.

A device which is used to help control the electrostatic charge buildup on a person is a body strap or wrist strap to be worn by the individual. The body straps are conductive on the surface contacting the skin surface and provide for an electrical connection point. An electrical ground cord may then be connected to the strap connecting the strap to an electrical ground potential, preferably through a predetermined limiting resistance usually built into the connector or the cord itself. So connected, such a body strap operates by draining any accumulated electrostatic charge on the individual to ground before the electrostatic charge buildup reaches dangerous levels.

One prior art body strap is described in U.S. Pat. No. 4,398,277, Christiansen et al, Conductive Elastomeric Body Strap, which is hereby incorporated by reference. Christiansen et al describes a body strap which is constructed from a band of fabric formed into a closed loop to encircle a body part, e.g., wrist, to which it is to be connected. The fabric is electrically conductive on the interior surface of the closed loop contacting the skin. A mechanical connection mechanism holds the loop of fabric in a fixed predetermined size. An electrical connection mechanism provides for an electrical connection between the conductive inner surface of the fabric to an electrical grounding cord which may be attached to the strap. The fabric is elastomeric to enable the body strap to expand to slip over the hand and still be snug around the wrist.

In the body strap described in Christiansen et al, the opposite ends of the fabric are permanently secured in the mechanical connector. The body of the connector has projections which grip the fabric and hold the fabric in the connector when the cover is secured. Thus, the resultant body strap formed is a fixed closed loop size. Since the fabric has a limit on the degree of its elastic nature, a range of sizes of closed loops for the body strap must be provided. This results in the necessity of stocking a plurality of differing sizes of body straps. Further, the elastomeric characteristics of the fabric generally means a fixed "life" of use of the fabric before its elastomeric or electroconductivity characteristics begin to break down. Since the fabric is secured in the connector at the factory, the replacement of the fabric requires replacement of the entire body strap.

The Charge-Guard 2200 series of static control wrist straps manufactured by Minnesota Mining and Manufacturing Company, St. Paul, Minnesota and marketed by Static Control Systems/3M, Austin, Texas is constructed generally as described in Christiansen et al (Charge-Guard is a registered trademark of Minnesota Mining and Manufacturing Company, St. Paul, Minnesota). In the Charge-Guard static control wrist straps, the ends of the projections 32, in Christiansen et al, are sonically welded after the fabric is in place to "mushroom" the ends of the projections in order to ensure that the fabric is secured in the connector.

U.S. Pat. No. 4,577,256, Breidegam, Woven Stretchable Grounding Strap, describes a wrist strap designed to be used to control electrostatic charge accumulations. The Breidegam strap has a clasp which allows its size to be adjusted. The adjustable clasp avoids the need to manufacture two or more models of the strap for different sized wrists. This does require that the strap be individually adjusted to fit snugly around the wrist of the individual wearer. If inadvertently or intentionally maladjusted, proper electrostatic protection may not be achieved. In the Breidegam strap, one end of the fabric is permanently secured into the clasp and held by plate and a rivet. Thus, one end of the fabric is fixed at the factory for the entire life of the strap. The second end of the fabric is engaged in the clasp by a pivotally mounted gate which when closed "jams" the fabric holding it in place, optionally with teeth to help the securing of the fabric. Typically, a pivotally mounted "jam" or "wedge" as is described in Breidegam is referred to as an "over-center" device. These devices operate by wedging the fabric between the jam member and a reaction member by using an eccentric pivot with a relatively long jam operating lever to gain the necessary leverage for the jam to work. One problem in a strap as described in Breidegam is that it does not allow for full 360 degree electrical contact with the skin and the fabric is electrically only connected at one end. Since electrical contact is only provided to the external ground cord from the one fixed end of the fabric, any charge contacting the inner surface of the fabric must travel around the strap in one direction only until reaching the fixed end. This requires, in some instances, a charge must follow only one path to travel almost entirely around the fabric before being connected to a ground strap. Since the electrical conductivity of the fabric, due to its elasticity, is typically the weakest link in a wrist strap grounding system, along with the fabric to skin contact, such one way only conductivity is a serious problem. Another problem with the Breidegam strap is that the pivotally mounted gate does not lend itself to economical manufacture. Because of the forces involved, the pivot points are required to be quite sturdily built.

SUMMARY OF THE INVENTION

The present invention provides a body or wrist strap useful for the control of electrostatic charge accumulation. The body strap provides adjustability without the use of expensive "over-center" jam mechanisms. The body strap provides for full 360 degree electrical contact with the skin and two parallel paths to ground, provides easy one-time, or repeated, adjustment by the individual user for trouble-free secure holding of the fabric ends and for the replacability of the fabric only, if desired.

Thus, the present invention provides for an adjustable, conductive body strap. The strap has a strip of material having a first end and a second end. The strip of material is electrically conductive on at least one surface, is elastomerically extensible in its longitudinal direction and is of at least a length to enable the strip of material to encircle a body part. A mechanical connector receives the first end and the second end of the strip of material to form a closed loop with the strip of material with the conductive surface formed toward the interior of the closed loop. The mechanical connector has a first part receiving the first end of the strip of material and has a second part receiving the second end of the strip material. The first part of the mechanical connector has a recess which receives the first end of the strip of material, the recess being formed with a plurality of spikes upon which the strip of material is impaled and secured. The second part of the mechanical connector has a plate over which the second end of the strip of material is passed. The plate has a plurality of spikes mounted on its surface upon which the strip of material may be impaled after the strip of material has been pulled to fit snugly around the body part. This second part of the mechanical connector further has a hinged cover which may be secured over the spikes of the plate trapping the strip of material thereon. An electrical connection mechanism is coupled to the strip of material for providing a connection point for an electrical cable capable of connecting the conductive body strap to ground. Preferably, the body strap further has a second cover secured to the first part of the mechanical connector securing the first end of the stip of material upon the spikes. Preferably, the second cover, back plate, is electrically conductive on its side which faces the strip of material. Preferably, the second cover also contacts the second end of the strip of material providing full 360 degree electrical continuity and full 360 degree electrical contact with the skin. Preferably, the hinged cover has transverse ridges spaced to pass on either side of the plate when the hinge cover is closed. Preferably, the transverse ridges force the strip of material into electrical contact with the second cover when the hinged cover is closed. Preferably, the hinged cover has a plurality of recesses receiving the tip of each of the spikes mounted on the plate. Preferably, the spikes have a zero draft profile facing the direction toward the second end of the strip of material. Preferably, the spikes are angled toward the second end of the strip of material. Preferably, the hinged cover of the mechanical connector is hingably attached at one side and, preferably, secured by means of a hook. Preferably, the hinged cover is releasably secured in a closed position by flexible hook, preferably opposite the hinge. Preferably, the electrical connection mechanism and the mechanical connection mechanism operate in conjunction with each other by means of the metallic plate, second cover, secured by means of a metallic stud formed to receive a snap connector. The metallic stud may be threaded and secured with a cooperating threaded member.

BRIEF DESCRIPTION OF THE DRAWINGS

The foregoing advantages, construction and operation of the present invention will become more readily apparent from the following drawings and accompanying description in which:

FIG. 9 illustrates an exploded isometric view of a preferred embodiment of the mechanical connector used in the adjustable conductive body strap of the present invention; and FIG. 10 illustrates a cross-section view of a preferred embodiment of the mechanical connector of the adjustable, conductive body strap of the present invention showing the mechanical connector in the closed position.

DESCRIPTION OF THE PREFERRED EMBODIMENTS

Figure 1:
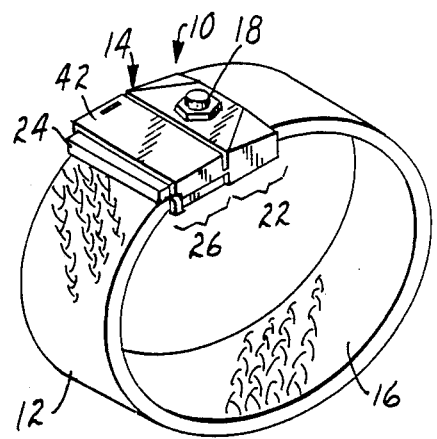
FIG. 1 illustrates an isometic view of the body strap of the present invention.

The adjustable, electrically conductive body strap 10 is illustrated in FIG. 1. The body strap 10 is formed into a closed loop designed to fit snugly around a portion of the body, e.g., a wrist or an ankle. The loop is formed by a strip of material 12 formed into a loop by connector 14. Connector 14 forms both the mechanical connection holding both ends of the strip of material 12 and the electrical connection mechanism providing a point for external connection of the body strap 10 to a ground potential. The interior surface 16 of the strip of material 12 is electrically conductive and should intimately contact the skin of the individual wearer of the body strap 10 when it is in position. Thus, electrostatic charges accumulating on the person of the wearer can be transported from the skin of the wearer to the conductive interior surface 16 of the body strap 10 transported to connector 14 and made available for conduction to ground through provision for connecting a grounding cord such as cord connector 18. Strip of material 12 may be formed of any suitable elastomeric electrically conductive material such as a fabric to form the band portion of the body strap 10. In a preferred embodiment, strip of material 12 is a knit fabric containing both elastomeric and electrically conductive fibers as described in Christiansen et al. Optionally, however, strip of material 12 could also be constructed from a stretch weave material such as is described in Breidegam. A first end 20 of the strip of material 12 is mechanically secured in a first part 22 of connector 14. The second end 24 of the strip of material 12 is adjustably secured in a second part 26 of connector 14.

Figure 4:
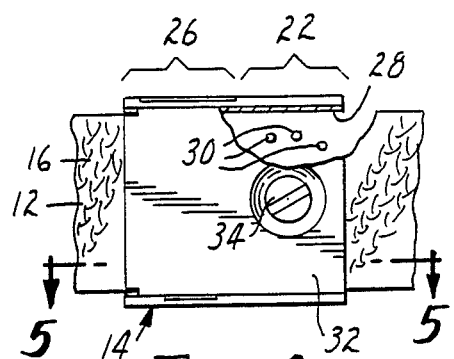
FIG. 4 illustrates a cutaway bottom view of the mechanical connector.
Figures 2, 3:
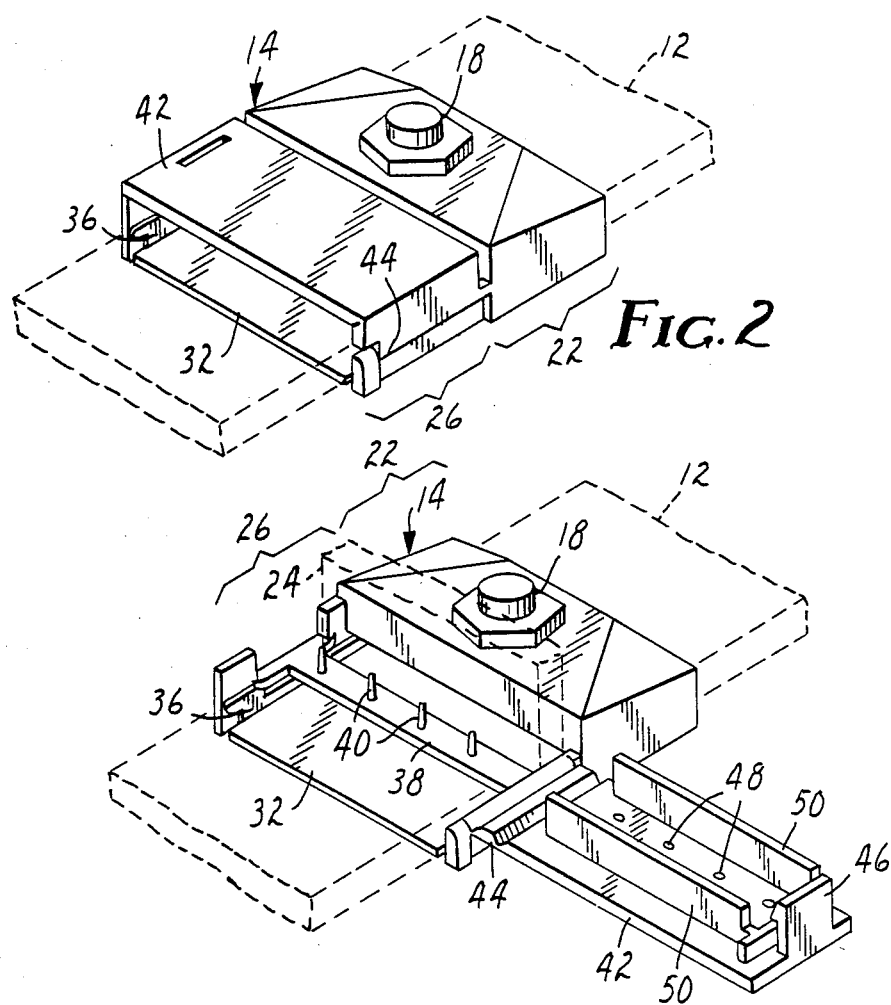
FIG. 2 illustrates a closeup of the mechanical connector in a closed position.
FIG. 3 illustrates a closeup of the mechanical connector in an open position.

The details of connector 14 are more readily illustrated in FIGS. 2 and 3. The first end 20 of the strip of material 12 is secured in the first part 22 of the connector 14. Secured in this manner the first end 20 is semi-permanently secured in that only disassembly of connector 14 can release first end 20 of the strip of material 12 from the connector 14. It is anticipated that body strap 10 can be shipped from the factory with the first end 20 of the strip of material 12 semi-permanently secured in the first part 22 of connector 14. This can be shown in better detail in FIG. 4 where the first end 20 and the strip of material 12 is formed into a recess 28 of the first part 22 of the connector 14. There the strip of material 12 is impaled upon a plurality of spikes 30 designed to secure first end 20 the strip of material 12 within the connector 14 when metallic back plate 32 which is secured in the connector 14 through a stud 34 and its cord connector 18 forming a snap connector. Stud 34 as well as cord connector 18 are metallic allowing for electrical conductivity from the interior surface 16 of the strip of material 12 to cord connector 18 and, of course, subsequently by external cord (not shown) to a ground potential. Metallic back plate 32 also preferably contacts the interior surface 16 of the second end 24 of the strip of material 12 to provide for full 360 degree electrical conductivity around body strap 10 and skin contact.

Figure 5:
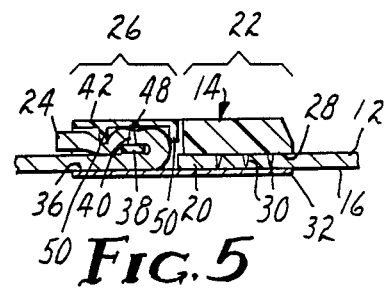
FIG. 5 illustrates a cross-section of the mechanical connector in a closed position.

Again referring to FIGS. 2 and 3, the second end 24 of the strip of material 12 is placed in the recess 36 in the second part 26 of connector 14. The second part 26 of connector 14 contains a transverse bar 38 upon which are mounted a plurality of spikes 40 extending outwardly from the transverse bar 38. The second end 24 of the strip of material 12 is passed under transverse bar 38 and pulled up on the far side of transverse bar 38 until the strip of material 12 is securely tightened around the body part with which it is to be utilized. When the strip of material 12 is suitably tight, the second end 24 of the strip of material 12 is then folded back over the top of transverse bar 38 and impaled upon spikes 40. Hinged cover 42 connected to the second part 26 of connector 14 by hinge 44 along one side, may then be closed over the top of the second end 24 of the strip material 12 and secured with a hook 46 securing hinged cover 42 in place and in turn securing the second end 24 of the strip of material 12 in the connector 14. The second end 24 of the strip of material 12 may be trimmed after the strip of material 12 is impaled upon spikes 40 and either before or after hinged cover 42 is secured in a closed position as illustrated in FIG. 2. Such trimming will prevent the existence of an electrically conductive surface on the exterior of the body strap 10. Preferably, hinged cover 42 contains a plurality of recesses 48 which cooperate with and receive the tips of spikes 40 when hinge cover 42 is in a closed position. The receiving of the tip of spikes 40 in recesses 48 will help prevent spikes 40 from bending, and subsequent release of the strip of material 12 from connector 14. Also preferably, hinged cover 42 has transverse ridges 50 so on one or both sides of transverse bar 38 to force the strip of material 12 into more intimate electrical contact with back plate 32 as can be illustrated from the cross-sectional view of FIG. 5. FIG. 5 also illustrates the impaling of the strip of material 12 upon spikes 30 and 40 as well as the electrical contact between back plate 32 and both the first end 20 and the second end 24 of the strip of material 12 forming full 360 degree electrical continuity around body strap 10 and skin contact. FIG. 5 illustrates the second end 24 of the strip of material 12 having been trimmed with a short portion of the second end 24 extending beyond the edge of hinged cover 42. Optionally, and preferably, second end 24 of the strip of material 12 will be trimmed at least flush with the edge of hinged cover 42 so that no electrically conductive surface is present on the exterior surface of body strap 10. Also preferably, the second end 24 of the strip of material 12 is not trimmed so short that some material is left to allow for a small amount of unraveling. In a preferred embodiment, the material forming connector 14 except for back plate 32, stud 34 and cord connector 18, is constructed from a plastic material preferably one that is static dissipative. In general, a material is static dissipative if it has a surface resistivity of between $10^8$ and $10^{14}$ ohms per square. Examples of material which could be utilized and which are static dissipative include hygroscopic nylon and carbon loaded polypropylene. As can be seen from examining FIGS. 2, 3 and 5 the second end 24 of the strip of material 12 is secured in connector 14 not only by spikes 40 and hinged cover 42 but also by the tortuous path in which the fabric is forced to take when passed first under and then back over transverse bar 38.

The hinged cover 42 holds the fabric 12 onto spikes 40. Further, transverse ridges 50 assist in holding the fabric 12 onto spikes 40 and help form the tortuous path.

Figure 6:
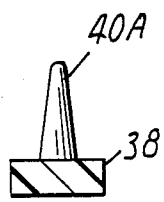
FIG. 6 illustrates one embodiment of the spikes used in the mechanical connector.
Figure 7:
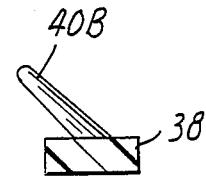
FIG. 7 illustrates another embodiment of the spikes used in the mechanical connector.
Figure 8:
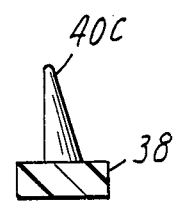
FIG. 8 illustrates another embodiment of the spikes used in the mechanical connector.

FIGS. 6, 7 and 8 are cross-sections illustrating various optional profiles of spikes 40 taken from a side view. In FIG. 6, spike 40A is of conical shape which is probably the most economical to manufacture and will provide an adequate job of securing strip of material 12 for most purposes. However, severe loading upon spike 40A will tend to lead toward the strip of material 12 rising up toward the end of spike 40A which results in larger lateral forces against spike 40 then otherwise would be encountered. Accordingly, spike 40C is illustrated in FIG. 8 is preferred. Spike 40C is also of conical shape but has a zero draft, i.e., vertical side, facing the extreme second end 24 of the strip of material 12. Spike 40C with one zero draft side is still economically manufacturable and since the side of the spike 40C which is loaded is vertical strip of material 12 will not tend to ride up toward the tip of the spike 40C and, thus, the lateral force on 40C will not be concentrated at its tip but rather more evenly over the entire length of spike 40C. This results in lower lateral forces on the tip of spike 40 than might otherwise be achieved with spike 40A as illustrated in FIG. 6. If still more lateral loading resistance is desired, then spike 40B as illustrated in FIG. 7 may be utilized. Spike 40B is angled toward the extreme end 24 of strip of material 12, in this case, 45 degrees, so that any lateral force on spike 40B will result in the strip of material 12 being forced more deeply onto to spike 40B and, thus, a more secure environment is provided. However, spike 40B probably is more difficult to manufacture.

FIGS. 9 and 10 illustrate a preferred embodiment of the mechanical connector 14A. Mechanical connector 14A illustrated in FIGS. 9 and 10 is similar to mechanical connector 14 illustrated in FIGS. 1 through 5. The path of the securing of the strip of material 12 differs between the two embodiments. With mechanical connector 12 as illustrated in FIGS. 1 through 5 strip of material 12 is passed first under transverse bar 38 and back over transverse bar 38 whereupon it is impaled upon spikes 40 by hinged cover 42. Mechanical connector 14A, illustrated in FIGS. 9 and 10, has a plate 52 in place of transverse bar 38. Strip of material 12 passes over plate 52 where it is impaled upon spikes 40 and secured with hinged cover 42. The second end 24 of strip of material 12 then passes from connector 14A adjacent to hinged cover 42 for which a space is provided next to the first part 22 of mechanical connector 14A. All other aspects of mechanical connector 14A are identical to corresponding aspects of mechanical connector 14. Note that in the mechanical connector 14A the inner surface 16 of the strip of material 12 is forced by transverse ridges 50 into contact with the metallic electrically conductive second cover, back plate, 32 providing full 360 degree electrical continuity and skin contact around the interior of the adjustable conductive body strap.

Optionally, mechanical connector 14A has an element, or bar, 54 positioned adjacent hinged cover 42 above the path of the second end 24 of the strip of material 12 before the strip of material 12 passes over plate 52. Element 54 is positioned transverse to strip of material 12 and provides a convenient fulcrum around which the strip of material 12 may be pulled when the strip of material is pulled tight around the body part (not shown) and before the strip of material 12 is secured over spikes 40 in plate 52.

Thus, it can be seen that there has been shown and described a novel adjustable, conductive body strap. It is to be recognized and understood, however, that various changes, modifications and substitution in the form and of the details of the present invention may be made by those skilled in the art without departing from the scope of the following claims.

What is claimed is:

1. An adjustable, conductive body strap, comprising:
    a strip of material having a first end and a second end, said strip of material being electrically conductive on at least one surface, being elastomerically extensible in its longitudinal direction, and being of at least a length to enable said strip of material to encircle a body part;
    a mechanical connector receiving said first end and said second end of said strip of material to form a closed loop with said strip of material with said at least one surface toward the interior of said closed loop, said mechanical connector having a first part receiving said first end of said strip of material and having a second part receiving said second end of said strip of material
    said first part of said mechanical connector having a recess receiving said first end of said strip of material, said recess being formed with a plurality of spikes upon which said strip of material is impaled and secured;
    said second part of said mechanical connector having a plate over which said second end of said strip of material is passed, said plate having a plurality of spikes upon which said strip of material may be impaled after said strip of material has been pulled tight around said body part, said second part of said mechanical connector further having a hinged cover for being secured over said spikes of said plate trapping said strip of material thereon;
    a second cover secured to said first part of said mechanical connector securing said first end of said strip of material upon said spikes; and
    electrical connection means coupled to said strip of material for making electrical contact with said at least one conductive surface and for providing a connection point for an electrical cable capable of connecting said conductive body strap to ground.

2. An adjustable, conductive body strap as in claim 1 wherein said hinged cover is releasably secured over said spikes.

3. An adjustable, conductive body strap as in claim 1 wherein said second cover is semi-permanently attached to said first part of said mechanical connector.

4. An adjustable, conductive body strap as in claim 1 wherein said second cover is electrically conductive on it side which faces said strip of material.

5. An adjustable, conductive body strap as in claim 4 wherein said second cover also contacts said second end of said strip of material providing a parallel path to ground and full 360 degree electrical skin contact and continuity.

6. An adjustable, conductive body strap as in claim 5 wherein said hinged cover has transverse ridges spaced to pass on either side of said plate when said hinged cover is closed.

7. An adjustable, conductive body strap as in claim 6 wherein said transverse ridges force said strip of material into electrical contact with said second cover when said hinged cover is closed.

8. An adjustable, conductive body strap as in claim 1 wherein said hinged cover has a plurality of recesses receiving the tip of each of said spikes mounted on said plate.

9. An adjustable, conductive body strap as in claim 1 wherein said spikes mounted on said plate have a zero draft profile facing the direction toward said second end of said strip of material.

10. An adjustable, conductive body strap as in claim 1 wherein said spikes mounted on said plate are angled toward said second end of said strip of material.

11. An adjustable, conductive body strap as in claim 1 wherein said hinged cover of said mechanical connector is hingeably attached at one side.

12. An adjustable, conductive body strap as in claim 11 wherein said hinged cover of said mechanical connector is secured by means of a hook.

13. An adjustable, conductive body strap as in claim 1 wherein said hinged cover is releasably secured in a closed position.

14. An adjustable, conductive body strap as in claim 13 wherein said hinged cover of mechanical connector is releasably secured by means of a flexible hook.

15. An adjustable, conductive body strap as in claim 14 which further comprises a transverse element incorporated in said second part of said mechanical connector, said adjustment stop element positioned transversely to and above said strip of material adjacent to said hinged cover.

16. An adjustable, conductive body strap as in claim 1 wherein said second cover of said mechanical connector is a metallic plate and is secured by means of a metallic stud formed to receive a snap connector, said metallic plate and metallic stud forming said electrical connection means.

17. An adjustable, conductive body strap as in claim 16 wherein said metallic stud is threaded and secured with a cooperating threaded member.

* * * * *